United States Patent [19]

Zumin Tricerri et al.

[11] 4,073,903
[45] Feb. 14, 1978

[54] 3-[5'(1-METHYLTETRAZOLYLTHIOMETHYL)]-7-[2(3''-NITROIMIDAZOLYL)ACETYL AMINO]CEPHALOSPORANIC ACID, SALTS, AND ITS PHARMACEUTICAL COMPOSITION

[75] Inventors: Silvia Zumin Tricerri, Carimate (Como); Lino Chiarani, Milan, both of Italy

[73] Assignee: Pierrel S.p.A., Milan, Italy

[21] Appl. No.: 726,833

[22] Filed: Sept. 27, 1976

[30] Foreign Application Priority Data

Oct. 1, 1975 United Kingdom ............... 40063/75

[51] Int. Cl.$^2$ .................. A61K 31/545; C07D 501/36
[52] U.S. Cl. ..................... 424/246; 544/27; 544/28
[58] Field of Search .................... 260/243 C; 424/246

[56] References Cited

U.S. PATENT DOCUMENTS

| | | | |
|---|---|---|---|
| 3,296,258 | 1/1967 | Vischer et al. | 260/243 C |
| 3,719,672 | 3/1973 | Heusler et al. | 424/246 |
| 3,804,832 | 4/1974 | Bickel et al. | 260/243 C |
| 3,865,820 | 2/1975 | Schorr et al. | 260/243 C |
| 4,008,230 | 2/1977 | Koppel | 260/243 C |
| 4,008,231 | 2/1977 | Wright | 260/243 C |
| 4,031,082 | 6/1977 | Chou | 260/243 C |

Primary Examiner—Nicholas S. Rizzo
Assistant Examiner—David E. Wheeler
Attorney, Agent, or Firm—Finnegan, Henderson, Farabow & Garrett

[57] ABSTRACT

The present invention relates to a novel therapeutically active derivative of 7-aminocephalosporanic acid which is 7-[1-(1H-4-nitroimidazolyl)acetyl]amino-3-[5-(1H-1-methyltetrazolyl)thio]methyl-3-cephem-4-carboxylic acid.

5 Claims, No Drawings

3-[5'(1-METHYLTETRAZOLYLTHIOMETHYL)]-7-[2(3''-NITROIMIDAZOLYL)ACETYL AMINO]CEPHALOSPORANIC ACID, SALTS, AND ITS PHARMACEUTICAL COMPOSITION

The present invention relates to a novel therapeutically active derivative of 7-aminocephalosporanic acid (7-ACA).

There is always a need for both improved and alternative antibacterial agents to be used in the treatment of infections caused by Gram-positive and Gram-negative organisms and this invention provides a new cephalosporin exhibiting high and broad spectrum anti-bacterial activity, useful as therapeutic agent in mammals, particulaly in man.

The compound of this invention is 7-[1-(1H-4-nitroimidazolyl)acetyl]amino-3-[5-(1H-1-methyltetrazolyl)thio]methyl-3-cephem-4-carboxylic acid and is represented by the structural formula

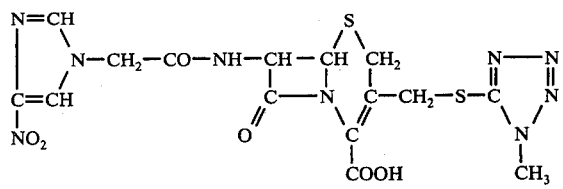

For convenience, this antibiotic is also referred to herein with the code number P-75123.

The compound of the present invention may be converted for pharmaceutical purposes into non-toxic pharmaceutically acceptable salts.

The acceptable non-toxic cations include metallic cations such as sodium and potassium, and substituted ammonium cations such as $(C_2H_5)_3 NH^+$.

The novel compound is a creamy white crystalline solid with a molecular weight of 481.47. It melts at 180° C.

The crystals are soluble in dimethylsulfoxide and practically insoluble in water.

The sodium salt is stable as a solid and is approximately 50% soluble in water.

The present invention also provides methods for the preparation of this new cephalosporin. The reaction scheme is exemplified below and comprises reacting a compound, or a salt thereof, of the formula:

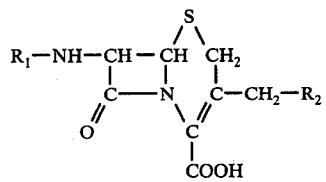

in which $R_1$ is a hydrogen atom or $Hal-CH_2-CO$, or 1-(1H-4-nitroimidazolyl)$-CH_2-CO$ and $R_2$ is the acetoxy or the 5-(1H-1-methyltetrazolyl)thio group:

a. When $R_1$ is 1-(1H-4-nitroimidazolyl)-$CH_2-CO$ and $R_2$ is acetoxy, with 1H-1-methyltetrazole-5-thiol or a metal salt thereof. (See Example 1).

b. When $R_1$ is hydrogen and $R_2$ is the 5-(1H-1-methyltetrazolyl)thio group, with a reactive derivative of the 1-(1H-4-nitroimidazolyl) acetic acid. (See Example 2).

c. When $R_1$ is $Hal-CH_2-CO$ and $R_2$ is the 5-(1H-1-methyltetrazolyl)thio group, with a metal salt of 4(5)-nitroimidazole. (See Example 3).

Every time the term Hal—(=halogen) is used, when not specifically indicated, it includes chlorine, bromine and the like.

All the starting compounds of formula II to be used in the invention may be prepared by a variety of methods.

The 7-[1-(1H-4-nitroimidazolyl)acetyl]amino cephalosporanic acid can be obtained by reacting a 7-ACA salt of a 7-ACA silyl derivative with a reactive derivative of the 1-(1H-4-nitroimidazolyl) acetic acid, or by reaction of a 7-haloacylated aminocephalosporanic acid with the 4(5)-nitroimidazole or its metallic salt in accordance with the procedure, for example, as described below under Example 4 to 6.

The 3-thiolated 7-ACA can be obtained by reacting 7-ACA with 1H-1-methyltetrazole-5-thiol (see Example 7).

the 7-amino-3-[5-(1H-1-methyltetrazolyl)thio]methyl-3-cephem-4-carboxylic acid can be reacted with a haloacetyl halide to obtain the 7-(1-haloacetyl)amino-3-[5-(1H-1-methyltetrazolyl)thio]methyl-3-cephem-4-carboxylic acid to be used as a starting compound, by means of the procedure, for example, as described below under Example 8.

The starting compound of formula II, wherein $R_1$ is 1-(1H-4-nitroimidazolyl)-$CH_2-CO$ and $R_2$ is acetoxy is preferably employed as a metal salt and is reacted with 1H-1-methyltetrazole-5-thiol or a metal salt thereof whereby it is converted into the desired compound of formula I.

The above reaction is preferably conducted in water or buffers, e.g., borate, phosphate buffer and the like.

The alternative starting compound of formula II, wherein $R_1$ is hydrogen and $R_2$ is the 5-(1H-1-methyltetrazolyl)thio group, is reacted with a reactive derivative of the 1-(1H-4-nitroimidazolyl) acetic acid to obtain the desired compound of formula I. The reaction is carried out in water and/or in an inert solvent, for example acetone, acetonitrile, methylene chloride and in the presence of a base, for example sodium bicarbonate, triethylamine and the like.

The 1-(1H-4-nitroimidazolyl) acetic acid is employed in a reactive form by the treatment with, for example, thionyl chloride, phosphorus oxychloride, phosphorus pentachloride and the like.

The alternative starting compound of formula II, wherein $R_1$ is $Hal-CH_2-CO$ and $R_2$ is the 5-(1H-1-methyltetrazolyl)thio group are reacted with a metal salt of 4(5)-nitroimidazole whereby it is converted into the desired compound of formula I.

The above reaction is carried out in an inert solvent, preferably dimethylformamide, and in the presence of a base, for example triethylamine. After the reaction is substantially complete, the compound of formula I is recovered from the reaction mixture in a free form by conventional techniques, for example, by evaporating the solvent and/or by adding water and adjusting the pH to 2.0 with diluted hydrochloric acid. The crude product can be further purified by conventional techniques, for example recrystallization, chromatography, trituration with appropriate solvent and the like.

The compound of formula I is preferably converted for pharmaceutical purposes into its pharmaceutically acceptable salts. The acceptable, non-toxic cations include metallic cations such as sodium, potassium and organic cations such as $(C_2H_5)_3 NH^+$.

The antibacterial compound according to the invention may be formulated for administration in any convenient way, by analogy with other antibiotics such as Cefazolin and the invention therefore includes within its scope a pharmaceutical composition comprising an antibacterial compound of formula I or a non-toxic derivative, e.g., salt thereof (as herein defined) adapted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multidose containers with an added preservative. The compositions may take such forms as suspensions, solution emulsions in oily or aqueous vehicles, and may contain formulatory agents such as suspending, stabilising and/or dispersing agents. Alternatively the active ingredient may be in powder form for reconstitution with a suitable vehicle, e.g., sterile, pyrogen-free water, before use.

The composition may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-liquid form, or may be used as drops, etc. Topical applications may be formulated in hydrophobic or hydrophilic bases as ointments, creams, lotions, paints, powders, etc.

For veterinary medicine the composition, may, for example, be formulated as an intramammary preparation in either long acting or quick-release bases.

The compositions may contain from 0.1% upwards, preferably from 10-60% of the active material, depending on the method of administration. Where the compositions comprise dosage units, each unit will preferably contain 50-500 mg. of the active ingredient. The dosage as employed for adult human treatment will preferably range from 100-3000 mg. for instance 1500 mg. per day, depending on the route and frequency of administration.

The compounds according to the invention may be administered in combination with other therapeutic agnets such as antibiotics, for example other cephalosporins, the penicillins or tetracyclines.

The cephalosporin of the present invention, i.e., the 7-[1-(1H-4-nitroimidazolyl)acetyl]amino-3-[5-(1H-1-methyltetrazolyl)thio]methyl-3-cephem-4-carboxylic acid (P-75123), has shown "in vitro" high antimicrobial activity against a wide spectrum of microorganisms both Gram-positive and Gram-negative.

In Table I the minimum inhibitory concentrations (MIC) of P-75123 against a variety of Gram-positive and Gram-negative bacteria are listed.

The sensitivity to the new Cephalosporin of the tested strains was determined by the standard twofold serial dilution method, using Tryptose Phosphate broth, Mueller Hinton broth, Todd Hewitt broth, or Tryptose Broth supplied by Difco.

The broth was inoculted with bacterial cells from an 18 hours culture in same broth, at 37° C. An inoculum of 0.1 ml (containing about $10^6$ cells/ml) was added to each tube giving a final volume of 5 ml. The final concentration of the cells in the broth was about $2.10^4$/ml. The test tubes were incubated at 37° C for 24 hours and the results were expressed as minimum inhibiting concentration (MIC), defined as the lowest concentration of antibiotic capable of hindering the growth of the microorganism.

TABLE I

7-[1-(1H-1-nitroimidazolyl)acetyl]amino-3-[5-(1H-1-methyltetrazolyl)thio]methyl-3-cephem-4-carboxylic acid

| Medium* | Test Organism** | Minimum inhibitory concentration (mcg/ml) |
|---|---|---|
| A | Staphylococcus aureus ATTC 653P | 0.195 |
| A | Staphylococcus aureus ISM 72/10 | 0.78 |
| C | Streptococcus mitis ATCC 9895 Ty V | 0.195 |
| C | Streptococcus bovis ATCC 15351 | 0.049 |
| C | Streptococcus uberis ATCC 9927 | 0.097 |
| A | Streptococcus faecalis ISM 66/54 | 100 |
| C | Diplococcus pneumoniae Ty XXVII-LRP 53 | 0.097 |
| A | Escherichia coli ATCC 19138 0 group 6 | 0.78 |
| A | Shigella dysenteriae ISM-LRP 41 | 0.78 |
| A | Shigella flexneri ISM-LRP 40 | 0.78 |
| A | Shigella sonnei ISM-LRP 5 | 1.56 |
| A | Enterobacter cloacae ISM 71/32 | > 100 |
| A | Enterobacter liquefaciens ISM 65/33 | 100 |
| A | Salmonella typhi ISM-LRP 8 | 0.78 |
| A | Salmonella typhimurium ISM-LRP 29 | |
| A | Arizona sp. ISM 67/9 | 0.78 |
| B | Serratia marcescens ISM 68/189 | 100 |
| A | Citrobacter freundii ISM 65/74 | 1.56 |
| A | Citrobacter freundii ISM 69/30 | 0.78 |
| A | Klebsiella pneumoniae ISM 68/67' 370 V' | 0.78 |
| B | Proteus morganii ISM-LRP 18 | 50 |
| B | Proteus rettgeri ISM-LRP 21 | 25 |
| B | Proteus mirabilis ATCC 10005 | 3.12 |
| B | Proteus mirabilis ISM 66/53 | 3.12 |
| D | Pasteurella multocida ATCC 6588 | 0.39 |
| D | Brucella abortus ISM-LRP 15 | 25 |
| D | Brucella suis ISM 66/35 | 12.5 |
| A | Pseudomonas aeruginosa ISM-LRP 9 | > 100 |

*Medium for determination of MIC
A Tryptose Phosphate Broth
B Mueller Hinton Broth
C Todd Hewitt Broth
D Tryptose Broth
**Numerals and letters following the names of the test microorganisms refer to strains.
a. Penicillin - sensitive strain
b. Penicillinase producing, penicillin-resistant strain.

In further testing, P-75123 was effective in inhibiting the growth of selected bacterial clinical isolates in the broth dilution test. Cefazolin, the sodium salt of 7-[1-(1H-tetrazolyl)acetyl]amino-3-[2-(5-methyl-1,3,4-thiodiazolyl)thio]methyl-3-cephem-4-carboxylic acid, was also included for comparative purposes.

In Table II, the MIC values exhibited by the two Cephalosporins against various clinical isolates of Klebsiella pneumoniae are compared.

TABLE II

| Test Organism* | | Minimum inhibitory concentration (mcg/ml) | |
|---|---|---|---|
| | | P-75123 | Cefazolin |
| Klebsiella pneumoniae | LRP 128 | 1.56 | 25 |
| " | LRP 129 | 0.39 | 3.12 |
| " | LRP 130 | 6.25 | 25 |
| " | LRP 131 | 3.12 | 25 |
| " | LRP 132 | 0.39 | 1.56 |
| " | LRP 133 | 0.78 | 1.56 |
| " | LRP 134 | 1.56 | 3.12 |
| " | LRP 135 | 3.12 | 25 |
| " | LRP 136 | 3.12 | 50 |
| " | LRP 137 | 0.78 | 0.25 |

*Lettered numbers following the names of the test microorganisms refer to strains.

In Table III, the MIC values exhibited by P-75123 and Cafazolin against various clinical isolates of Escherichia coli are listed.

TABLE III

| Test Organism* | | Minimum inhibitory concentration (mcg/ml) | |
|---|---|---|---|
| | | P-75123 | Cefazolin |
| *Escherichia coli* | LRP 87 | 3.12 | 25 |
| " | LRP 94 | 1.56 | 6.25 |
| " | LRP 96 | 1.56 | 6.25 |
| " | LRP 110 | 0.78 | 6.25 |
| " | LRP 143 | 0.78 | 1.56 |
| " | LRP 150 | 1.56 | 12.5 |
| " | LRP 151 | 1.56 | 12.5 |
| " | LRP 152 | 50 | 100 |
| " | LRP 154 | 1.56 | 3.12 |
| " | LRP 155 | 1.56 | 1.56 |
| " | LRP 156 | 1.56 | 6.25 |
| " | LRP 158 | 1.56 | 25 |
| " | LRP 159 | 0.78 | 1.56 |
| " | LRP 163 | 1.56 | 3.12 |

*Lettered numbers following the names of the test microorganisms refer to strain In Table IV, the MIC values exhibited by the two Cephalosporins, P-75123 and Cefazolin, against various clinical isolates of Ampicillin-resistant strains of Salmonella spp. are compared.

TABLE IV

| Test Organism* | | Minimun inhibitory concentration (mcg/ml) | |
|---|---|---|---|
| | | P-75123 | Cefazolin |
| *Salmonella essen* | LRP 139 | 1.56 | 6.25 |
| *Salmonella wien* | LRP 138 | 3.12 | 25 |
| *Salmonella wien* | LRP 140 | 6.25 | 50 |
| *Salmonella wien* | LRP 141 | 6.25 | 100 |
| *Salmonella heidelberg* | LRP 142 | 1.56 | 12.5 |

*Lettered numbers following the names of the test microorganisms refer to strain.

The new Cephalosporin (P-75123) has shown also very good activity "in vivo", in treatment of systemically infected mice. Charles River CD 1 female mice, weighing 18 to 20 grams, were challenged intraperitoneally with 0.5 ml of a bacterial suspension containing sufficient organisms to kill untreated animals within 24 hours.

The animals were treated subcutaneously in accordance with the footnote at Table V.

The number of mice surviving the challenge for seven days was recorded and $ED_{50}$ - the dose in mg/Kg required to protect half the infected animals from death - was then estimated by the method of Reed L. J. and Muench H. (Amer. J. Hyg., 27, 493–497, 1938). Comparative tests with Cefazolin were run under the same condition.

In Table V, the efficacy of the intramuscular treatment of mice systemically infected with Klebsiella pneumoniae and Escherichia coli are recorded.

TABLE V

| Test Organism* | | $ED_{50}$ per treatment (mg/Kg)** | |
|---|---|---|---|
| | | P-75123 | Cefazolin |
| *Klebsiella pneumoniae* | LRP 128 | 49 | 90 |
| *Escherichia coli* | LRP 151 | 35 | 35 |

*Numerals and letters following the names of the test microorganisms refer to strains.
**Animals were treated at 1, 4 and 7 hours after infection.

The following examples are intended to illustrate the methods for the preparation of the product of the invention.

It is to be understood they are not to be considered as limitative.

Thin layer chromatography was performed with 0.25 mm chromatoplates of silica gel $GF_{254}$ supplied by Merck. Ir spectra were recorded on a Perkin Elmer 257 spectrophotometer and nmr spectra were determined on a Varian 60 MHz with TMS as an internal standard. Melting points are not given in the examples. The purity, evaluated by tlc (thin layer chromatography), ir (infrared spectrum), nmr (nuclear magnetic resonance), and determined by titration was about 90 ± 5% for each product.

EXAMPLE 1

A solution of 1.35 g of sodium 7-[1-[1H-4-nitroimidazolyl)acetyl]amino cephalosporanate and 0.580 g of 1H-1-methyltetrazole-5-thiol in 30 ml of phosphate buffer (pH 6.4) was stirred for 8 hours at 60° C followed by standing overnight. The solution was filtered and the pH adjusted to 5.2. After washing with ethyl acetate the aqueous layer was acidified to pH 2 with 4N hydrochloric acid. The precipitate was filtered and the filter cake washed with water, triturated with ether and dried in vacuo ver $P_2O_5$.

The crude powder (1.1 g) was nearly pure 7-[1-(1H-4-nitroimidazolyl)acetyl]amino-3-[5-(1H-1-methyltetrazolyl)thio]methyl-3-cephem-4-carboxylic acid. The product was crystallized from ethanol/acetone/water (1:1:0.2) to produce nearly colorless prisms which contain 1⅓ mole of crystallization water.

Only one spot on tlc with acetone/chloroform/acetic acid (8:2:1); m.p. 180° C; $\lambda_{max}^{NaHCO_3O,1N}$ 275 nm, $A_{1\,cm}^{1\%}$ 285; $[\alpha]_D^{25}$ +55°, (c=1, $NaHCO_3$ O,5N); ir (KBr), 1780 (β-lactam); nmr δ (dimethylsulfoxide-$d_6$), 8.18 (d,5-H,imidazole), 7.68 (d,2-H,imidazole), 4.92 (s,N—$CH_2$), 3.92 (s,N—$CH_3$).

EXAMPLE 2

To a stirred solution of 3.28 g of 7-amino3-[5-(1H-1-methyltetrazolyl)thio]methyl-3-cephem-4-carboxylic acid and 2.5 g of sodium bicarbonate in 30 ml of water and 15 ml of acetone cooled in an ice-water mixture were added 2.28 g of 1-(1H-4-nitroimidazolyl)acetylchloride during a period of 10 minutes.

After stirring for 2 hours at 0° C–5° C and for additional 2 hours at room temperature, the pH was adjusted to 5.5 with N hydrochloric acid and the reaction mixture was extracted with ethyl acetate. The aqueous layer was acidified to pH 2 with N hydrochloric acid.

The resulting precipitate was filtered, washed with ice-water and ether and dried in vacuo over $P_2O_5$ to give crude 2.5 g of the same product as in Example 1.

EXAMPLE 3

A solution of 2.25 g of 7-(bromoacetyl)amino-3-[5-(1H-1-methyltetrazolyl)thio]methyl-3-cephem-4-carboxylic acid, 0.800 g of 4(5)-nitroimidazole sodium salt and triethylamine in 15 ml of dimethylformamide was stirred for 60 minutes at 0° C and overnight at room temperature.

The reaction mixture was then poured in 30 ml $H_2O$ and extracted with ethyl acetate. The aqueous layer was acidified to pH 2 with 2N hydrochloric acid and extracted with two 100 ml of ethyl acetate. The organic layer was washed with water, dried over sodium sulfate and concentrated under reduced pressure leaving an oily residue which was treated with ether-petrol ether (1:1) to obtain 2.0 g of the same product as in Example 1.

EXAMPLE 4

To a stirred solution of 0.762 g of 7-aminocephalosporanic acid and 7.5 ml of $Et_3N$ O,4N (in $H_2O$) in 14 ml of acetone and 7.5 ml of water cooled to −5° C were added 0.700 g of 1-(1H-4-nitroimidazolyl)acetylchloride during a period of 60 minutes. The pH was maintained at 6.7 with Et₃N—H₂O (1:1). The resulting mixture was stirred for 2 hours at 0° C–5° C and concentrated under reduced pressure leaving an aqueous layer which was filtered and adjusted to pH with N hydrochloric acid. The formed precipitate was filtered, triturated with ether and dissolved in 10% bicarbonate aqueous solution.

The aqueous solution was adjusted to pH 3 with 10% hydrochloric acid, filtered and adjusted to pH 2. The formed precipitate was collected by filtration and washed with water and dried to obtain nearly pure 7-[1-(1H-4-nitroimidazolyl)acetyl]amino cephalosporanic acid. Only one spot with acetone/chloroform/acetic acid (8:2:1); nmr δ (dimethyl-sulfoxide-d₆), 8.18 ($d$,J$_{25}$=1.5 cps, 5-H, imidazole), 7.70 ($d$,J$_{25}$=1.5 cps, 2—H, imidazole), 4.95 ($s$,N—CH₂); ir (KBr), 1775 (β-lactam).

EXAMPLE 5

2.5 g of 1-(1H-4-nitroimidazolyl)acetylchloride were added during a period of 45 minutes to a stirred and cooled (−5° C) mixture of silylated 7-aminocephalosporanic acid [prepared from 2.92 g of 7-aminocephalosporanic acid, 0.86 ml of Me₃SiCl and 1.44 ml of (me₃Si)₂NH] in 40 ml of anhydrous 1,2-dichloroethane containing 1.6 ml of N,N-dimethylaniline.

After stirring for 30 minutes at 0° C and for 1 hour at room temperature, the reaction mixture was poured into 60 ml of cooled water under vigorous stirring to obtain a precipitate. It was collected by filtration and dissolved into aqueous sodium bicarbonate. The filtered aqueous layer was adjusted to pH 2 with 10% hydrochloric acid to form a precipitate which was filtered, dried and triturated with ether to obtain 2.27 g of the same product as in Example 4.

EXAMPLE 6

To a solution of 2.94 g of 7-(bromoacetyl)amino cephalosporanic acid and 1.08 ml of triethylamine in 21 ml of dimethylformamide was added 1.5 g of 4(5)-nitroimidazole sodium salt. The mixture was stirred for 4 hours at 0° C–5° C, filtered and poured into 42 ml of cooled water.

After adjusting the pH value of the solution to 2 with 4N hydrochloric acid, the formed precipitate was collected, washed with water, triturated with ether and dissolved in 10% aqueous sodium bicarbonate.

The aqueous solution was filtered and adjusted to pH 2.

The precipitate, collected by filtration, was washed with water and dried to obtain 2.46 g of the same product as in Example 4.

EXAMPLE 7

To a suspension of 2.72 g of 7-aminocephalosporanic acid in 20 ml of water and 10 ml of acetone were added 1.89 g of NaHCO₃ in 20 ml of water, and the resultant solution was heated to 40°–50° C. 1.45 g of 1H-1-methyltetrazole-5-thiol in 20 ml of acetone was added and the solution was stirred for 2 hours at room temperature and for 7 hours at 60° C. The pH was maintained between 7.4 – 7.8 by the addition of 1% NaHCO₃ or NHCl if necessary. When the reaction was complete the solution was cooled to +2° C and acidified to pH 3.5.

The formed precipitate was collected by filtration and washed with water and acetone and dried. The crude product (2.2 g) was purified by suspending in 30 ml of water and adding 2.3 ml 6 N HCl.

The acidic suspension was stirred at room temperature for 90 minutes (the nmr spectrum showed no acetoxy remaining).

After filtration through Celite the filtrate was cooled and adjusted to pH 3.5 with 15% NaOH. The precipitate was filtered, washed with water and acetone and dried. Yield 1.3 g.

Only one spot with acetone/chloroform/acetic acid (8:2:1) for the obtained 7-amino-3-[5-(1H-1-methyltetrazolyl)thio]methyl-3-cephem-4-carboxylic acid.

EXAMPLE 8

To a suspension of 7.28 g of 7-amino-3-[5-(1H-1-methyltetrazolyl)thio]methyl-3-cephem-4-carboxylic acid in 55 ml of water and 20 ml of acetone were added 5.44 g of NaHCO₃. The solution was cooled to +3° C and 5.44 g of bromoacetyl bromide were added under rapid stirring.

The mixture was stirred for 60 minutes at 20° C and then the pH value was adjusted to 4 with H₃PO₄ 40%. After filtering through Celite the filtrate was cooled and adjusted to pH 2 with H₃PO₄ 40%. The mixture was extracted with ethyl acetate 3 × 100 ml. The organic layer was washed, dried and evaporated in vacuo to give a residue which was triturated with ether.

Yield 5.4 g of 7-(bromoacetyl)amino-3-[5-(1H-1-methyltetrazolyl(thio]methyl-3-cephem-4-carboxylic acid.

Only one spot with acetone/chloroform/acetic acid (8:2:1).

EXAMPLE 9

To a suspension of 16 g of 7-[1H-4-nitroimidazolyl)acetyl]amino-3-[5-(1H-1-methyltetrazolyl)thio]methyl-3-cephem-4-carboxylic acid in 800 ml of methanol were added 25.6 ml of NaOH 5% in methanol.

The solution was filtered and evaporated. The residue was triturated with acetone, collected by filtration and dried over P₂O₅ under reduced pressure for one day.

Yield 14.5 g.

The colorless salt contains 1.7% water.

What is claimed is:

1. A cephalosporin compound of the formula

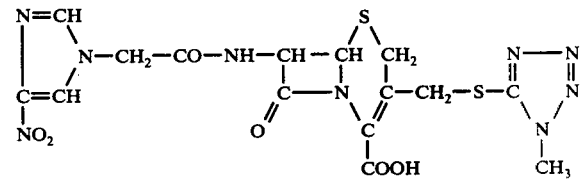

or non-toxic, pharmaceutically acceptable salts thereof.

2. The sodium salt of the compound of claim 1.

3. The potassium salt of the compound of claim 1.

4. The substituted ammonium salts of the compound of claim 1.

5. A pharmaceutical composition comprising the antibacterial compound of claim 1 and a pharmaceutical carrier or excipient.

* * * * *

UNITED STATES PATENT AND TRADEMARK OFFICE
CERTIFICATE OF CORRECTION

PATENT NO. : 4,073,903
DATED : February 14, 1978
INVENTOR(S) : SILVIA ZUMIN TRICERRI ET AL.

It is certified that error appears in the above-identified patent and that said Letters Patent are hereby corrected as shown below:

Please change the title on the cover and in Col. 1 of the patent, as follows:
--3-desacetoxymethyl-3-[5-(1-methyltetrazolyl)thio]
methyl-7-[1-(4-nitroimidazolyl)acetyl]aminocephalosporanic
acid--.

Col. 2, line 20, change "the" to --The--.
Col. 3, line 47, change "agnets" to --agents--.
Col. 4, Table I, first microorganism, change "ATCC 653P" to --ATCC 6538P$^a$--.
Col. 4, Table I, second microorganism, change "72/10" to --72/10$^b$--.
Col. 4, Table I, 15th microorganism, add --0.78-- under MIC value column.
Col. 6, first line of Example 2, change "7-amino3" to --7-amino-3--.
Col. 7, line 5, change "to pH" to --to pH 2--.
Col. 7, line 25, change "(me$_3$Si)$_2$NH" to --(Me$_3$Si)$_2$NH--.
Col. 7, line 66, change "NHCl" to --N HCl--.
Col. 8, line 31, change "tetrazolyl(thio]" to --tetrazolyl)thio]--.
Col. 8, first line of Example 9, change "7-[1H-4" to --7-[1-(1H-4--.

Signed and Sealed this

Twenty-seventh Day of March 1979

[SEAL]

Attest:

RUTH C. MASON
Attesting Officer

DONALD W. BANNER
Commissioner of Patents and Trademarks